(12) United States Patent
Linke et al.

(10) Patent No.: US 11,312,954 B2
(45) Date of Patent: Apr. 26, 2022

(54) TRANSKINGDOM PLATFORM FOR THERAPEUTIC NUCLEIC ACID DELIVERY

(71) Applicant: SIVEC BIOTECHNOLOGIES, LLC, Fort Collins, CO (US)

(72) Inventors: Lyndsey M. Linke, Windsor, CO (US); Darcy Mora, Fort Collins, CO (US)

(73) Assignee: SiVEC Biotechnologies, LLC, Fort Collins, CO (US)

( * ) Notice: Subject to any disclaimer, the term of this patent is extended or adjusted under 35 U.S.C. 154(b) by 72 days.

(21) Appl. No.: 16/591,782

(22) Filed: Oct. 3, 2019

(65) Prior Publication Data
US 2020/0102558 A1 Apr. 2, 2020

Related U.S. Application Data

(63) Continuation of application No. PCT/US2018/025961, filed on Apr. 3, 2018.

(60) Provisional application No. 62/480,875, filed on Apr. 3, 2017.

(51) Int. Cl.
| | |
|---|---|
| *C07H 21/04* | (2006.01) |
| *C12N 15/11* | (2006.01) |
| *C07K 14/11* | (2006.01) |
| *C07K 14/245* | (2006.01) |
| *C12N 1/20* | (2006.01) |
| *C12N 15/70* | (2006.01) |
| *C12R 1/19* | (2006.01) |

(52) U.S. Cl.
CPC ............ *C12N 15/111* (2013.01); *C07K 14/11* (2013.01); *C07K 14/245* (2013.01); *C12N 1/20* (2013.01); *C12N 1/205* (2021.05); *C12N 15/70* (2013.01); *C12N 2310/141* (2013.01); *C12N 2760/16122* (2013.01); *C12N 2760/16151* (2013.01); *C12R 2001/19* (2021.05); *C12Y 201/01* (2013.01)

(58) Field of Classification Search
None
See application file for complete search history.

(56) References Cited

U.S. PATENT DOCUMENTS

| | | |
|---|---|---|
| 8,475,807 B2 | 7/2013 | Perez |
| 2001/0036463 A1 | 11/2001 | Compans et al. |
| 2006/0160759 A1 | 7/2006 | Chen et al. |
| 2007/0099858 A1 | 5/2007 | Jadhav et al. |
| 2010/0092438 A1 | 4/2010 | Fruehauf et al. |
| 2010/0144843 A1 | 6/2010 | McSwiggen et al. |
| 2010/0189691 A1 | 7/2010 | Fruehauf et al. |
| 2010/0204297 A1 | 8/2010 | Chen et al. |
| 2011/0111481 A1 | 5/2011 | Li |
| 2011/0150912 A1 | 6/2011 | Perez |
| 2011/0209231 A1 | 8/2011 | Doran et al. |
| 2012/0101045 A1 | 4/2012 | Dowdy et al. |
| 2013/0225651 A1 | 8/2013 | Zheng et al. |
| 2016/0177296 A1 | 6/2016 | Linke et al. |
| 2019/0284559 A1 | 9/2019 | Linke et al. |

FOREIGN PATENT DOCUMENTS

| | | |
|---|---|---|
| WO | WO2008/138072 A1 | 11/2008 |
| WO | WO2015112873 A1 | 7/2015 |

OTHER PUBLICATIONS

Aigner, Achim. "Transkingdom RNA interference (tkRNAi) as a new delivery tool for therapeutic RNA." Expert opinion on biological therapy 9.12 (2009): 1533-1542.*
Keates, Andrew C., et al. "TransKingdom RNA interference: a bacterial approach to challenges in RNAi therapy and delivery." Biotechnology and Genetic Engineering Reviews 25.1 (2008): 113-128.*
Dykxhoorn, Derek M., and Judy Lieberman. "Silencing viral infection." PLoS medicine 3.7 (2006): e242.*
And Li, Tiejun, et al. ("Development of RNA interference-based therapeutics and application of multi-target small interfering RNAs." Nucleic acid therapeutics 24.4 (2014): 302-312).*
Nguyen T.A., Fruehauf J.H. (2009) transkingdom RNA Interference (tkRNAi): A Novel Method to Induce Therapeutic Gene Silencing. In: De Libero G. (eds) T Cell Protocols. Methods in Molecular Biology™, vol. 514. Humana Press. https://doi.org/10.1007/978-1-60327-527-9_3.
Linke LM, Wilusz J, Pabilonia KL, Fruehauf J, Magnuson R, Olea-Popelka F, Triantis J, Landolt G, Salman M. Inhibiting avian influenza virus shedding using a novel RNAi antiviral vector technology: proof of concept in an avian cell model. AMB Express. Mar. 2016;6(1):16. doi: 10.1186/s13568-016-0187-y. Epub Feb. 24, 2016. PMID: 26910902; PMCID: PMC4766140.
Xiang S, Fruehauf J, Li CJ. Short hairpin RNA-expressing bacteria elicit RNA interference in mammals. Nat Biotechnol. Jun. 2006;24(6):697-702. doi: 10.1038/nbt1211. Epub May 14, 2006. PMID: 16699500.
Nguyen TA, Fruehauf JH. Transkingdom RNA interference (tkRNAi): a novel method to induce therapeutic gene silencing. Methods Mol Biol. 2009;514:27-34. doi: 10.1007/978-1-60327-527-9_3. PMID: 19048211.
Lage H, Krühn A. Bacterial delivery of RNAi effectors: transkingdom RNAi. J Vis Exp. Aug. 18, 2010;(42):2099. doi: 10.3791/2099. PMID: 20811323; PMCID: PMC3156018.

(Continued)

*Primary Examiner* — Kimberly Chong
(74) *Attorney, Agent, or Firm* — Michael M. McGaw; McGaw Law, P.C.

(57) ABSTRACT

A transkingdom platform for the delivery of therapeutic nucleic acids to epithelial tissues where the nucleic acids are designed to have enhanced stability. The platform offers numerous improvements to prior delivery platforms including expression of the double-stranded RNA binding domain (dsRBD) domains of TAR RNA binding protein (TRBP), knockout of RNase R activity in the bacterial delivery vehicle, and expression of the methyltransferase gene, HEN1, for simultaneous packaging with a therapeutic nucleic acid delivery vehicle.

29 Claims, 6 Drawing Sheets

(56) References Cited

OTHER PUBLICATIONS

Wang W, DeFeo CJ, Alvarado-Facundo E, Vassell R, Weiss CD. Intermonomer Interactions in Hemagglutinin Subunits HA1 and HA2 Affecting Hemagglutinin Stability and Influenza Virus Infectivity. J Virol. Oct. 2015;89(20):10602-11. doi: 10.1128/JV100939-15. Epub Aug. 12, 2015. PMID: 26269180; PMCID: PMC4580181.
Palumbo RN, Wang C. Bacterial invasin: structure, function, and implication for targeted oral gene delivery. Curr Drug Deliv. Jan. 2006;3(1):47-53. doi: 10.2174/156720106775197475. PMID: 16472093.
Youngren-Ortiz, Susanne R et al. "Aerosol Delivery of siRNA to the Lungs. Part 1: Rationale for Gene Delivery Systems." Kona : powder science and technology in Japan vol. 33 (2016): 63-85. doi:10 14356/kona.2016014.
Krühn A, Wang A, Fruehauf JH, Lage H. Delivery of short hairpin RNAs by transkingdom RNA interference modulates the classical ABCB1-mediated multidrug-resistant phenotype of cancer cells. Cell Cycle. Oct. 15, 2009;8(20):3349-54. doi: 10.4161/cc.8.20.9845. Epub Oct. 18, 2009. PMID: 19770582.

\* cited by examiner

| | Without Modification | | RNase R Knockout | |
|---|---|---|---|---|
| Incubation Temperature | 37°C | < 37°C | 37°C | < 37°C |
| dsRNA concentration | Low | High | Low | High |
| RNase R Activity | Low | High | None | None |
| Resulting [dsRNA] availability | Low | Low | Low | High |

RNase R dsRNA (shRNA as example)

Nucleotides/dsRNA fragments resulting from degradation by RNase R

FIG. 6 ary application is to express a methyltransferase gene, such as HEN1, for simultaneous packaging within the delivery
TRANSKINGDOM PLATFORM FOR THERAPEUTIC NUCLEIC ACID DELIVERY

CROSS-REFERENCE TO RELATED APPLICATIONS

This application is a continuation of International Patent Application No. PCT/US2018/025961, filed Apr. 3, 2018, which claims the benefit of U.S. Provisional Application No. 62/480,875, filed Apr. 3, 2017.

FIELD OF INVENTION

This invention relates to treatment and prevention of disease. More specifically, this invention relates to a transkingdom platform with improved invasive properties for the delivery of therapeutic nucleic acids to epithelial tissues where the transkingdom platform has been engineered to produce the nucleic acids with enhanced stability.

BACKGROUND OF THE INVENTION

The therapeutic applications of nucleic acids (NAs) have strong potential for a wide range of clinical targets. However, the delivery of NAs to specific cells and tissues, and their transient targeting effects, remain major obstacles to harnessing their capabilities and clinical application.

Ribonucleic acid (RNA)-interference (RNAi) is a technology that specifically inhibits gene expression. It is carried out by small, double-stranded small interfering RNA (siRNA) or short hairpin RNA (shRNA) often having lengths of approximately 21-27 nucleotides.

The effectiveness of siRNA and shRNA can be limited by a number of factors. First, siRNA and shRNA are easily degraded by ribonucleases (RNases), reducing their efficacy. Second, they are unable to permeate cell membranes, making their bioavailability very low. Since siRNAs are unable to cross cell membranes independently, a delivery vehicle is often employed, such as viral vectors and synthetic carriers. These viral and synthetic siRNA vehicles pose serious limitations and concerns for clinical efficacy, such as cell death, RNAi/microRNA saturation and hepatotoxicity, and tumorigenesis. Synthetic vehicles often have low delivery efficiencies and require large doses to achieve clinical efficacy, which can be cost-prohibitive and often toxic. Additionally, siRNA-based applications are historically associated with transient RNAi effects, meaning the silencing effect required for clinical targeting is short-lived. While chemical modification of shRNA/siRNA and the application of numerous nanotechnology-based delivery approaches have been pursued, the limited delivery efficiencies to a narrow number of target tissues, as well as the short-lived effect of RNAi, remain major roadblocks. A delivery platform for targeted intracellular delivery of RNAi mediating agents and other nucleic acids, including deoxyribonucleic acids (DNA), ribonucleic acids (RNA), small interfering RNA/short hairpin RNA (siRNA/shRNA), micro RNA (miRNA), antagomiRs, aptamers, messenger RNA (mRNA), splice-switching oligonucleotides, defective interfering particles, and antisense oligonucleotides, to specific tissues is essential to capitalizing on the therapeutic potential that nucleic acid-based technologies hold for translational medicine. The present invention provides such delivery platforms as presented in the following disclosure.

SUMMARY OF THE INVENTION

Transkingdom NA delivery vehicles are significantly advanced through the employment of several unique features taught herein. The present invention provides a modified transkingdom delivery system with numerous significant and substantial features and/or advancements to prior delivery platforms. A first advancement is to express the double-stranded RNA-binding domains (dsRBDs) of a double-stranded RNA-binding protein (dsRBP) such as transactive response (TAR) RBP (TRBP) for simultaneous packaging within the transkingdom delivery vehicle. The justification behind this innovation is that dsRBPs such as TRBP bind dsRNAs with high affinity and provide protection against RNA degradation, provide stabilization of miRNA precursors, and serve as an important component of siRNA and miRNA mediated gene silencing. A second advancement is to knockout RNase R activity in the bacterial delivery vehicle. The justification behind this modification is that following bacterial cell exponential growth, when shRNA generation is maximized, halting bacterial growth and incubating the cultures below 37° C. will inhibit double stranded (ds) RNA decay, thereby enhancing the stability of the encoded therapeutic shRNAs. A third advancement is to express a methyltransferase gene, such as HEN1, for simultaneous packaging within the delivery vehicle. The justification behind this modification is that methylation of the 3' terminal nucleotide, as provided by a methyltransferase such as HEN1, protects against 3'-5' degradation and 3' uridylation of siRNA, ultimately increasing the stability of the siRNAs for enhanced RNAi. Additional improvements and advancements are described below. These proposed improvements each represent a unique approach to enhancing shRNA stability and the therapeutic longevity of the siRNAs.

The technology taught herein offers numerous advantages over current state-of-the art platforms and other NA based delivery applications including: (1) Targeted delivery to mucosal epithelial tissues with efficient intracellular delivery and endosomal escape; (2) Stable delivery of shRNA payloads for catalytic and persistent RNAi silencing; (3) Elimination of expensive synthetic siRNA manufacturing; (4) Adaptable clinical administration for oral, intranasal, ocular, vaginal, rectal, and respiratory dosing; (5) Utilizes a naturally derived vehicle with a confirmed safety record for clinical purposes (non-irritating to delicate mucosal tissues); (6) Rapid scale-up for disease readiness during emergency outbreaks (i.e. pandemic flu); (7) Feasible therapeutic application for infectious, immunologic and allergic diseases; (8) Could be used in conjunction with existing vaccination, antibiotic, antiviral, etc. regimens; (9) Eliminates need for permeation enhancers which can increase risk for toxin and pathogen invasion; (10) NAs are generated by prokaryotic RNA polymerase and delivered in a sequence-independent manner making this a versatile platform for delivery of any NA-based therapeutic alone or in combination (i.e. siRNA/shRNA, miRNA, antagomiRs, aptamers, mRNA, splice-switching oligonucleotides, defective interfering particles, antisense oligonucleotides).

This novel approach provides a new perspective on NA delivery and addresses many of the shortcomings associated with current NA delivery approaches. In general, the improvements taught herein enhance the functionality of the transkingdom delivery vehicles for numerous uses including therapeutic applications by: (a) improving the stability of the NAs that are generated and delivered, such as by expressing the HEN1 and TRBP and providing an RNase R knockout, (b) improving stability of the transkingdom delivery vehicles themselves, such as by putting gene expression of certain genes (e.g. inv, hlyA, HEN1, TRBP, and/or HA-1 genes) on the chromosome rather than on the plasmid, thereby improving the stability of the delivery vehicles and making manufacturing easier, (c) improving the invasive properties of the delivery vehicles (e.g. by including HA-1 and by expressing both HA-1 and inv from the chromosome rather than by plasmid, though expression from the plasmid of these genes is also contemplated herein), (d) removing the need for antibiotic selection which is not ideal for manufacturing/regulation or for therapeutic applications. All of these modifications act synergistically to improve the functionality of transkingdom NA delivery system for therapeutic applications.

In a first aspect the present invention provides a nonpathogenic bacterium or yeast comprising a prokaryotic or eukaryotic vector, as appropriate. The vector includes a DNA molecule encoding one or more therapeutic nucleic acids (e.g. short double stranded RNAs) and a promoter to control transcription of the short double stranded RNAs, wherein the short double stranded RNAs interfere with one or more target RNA molecules and wherein the bacterium is engineered to express one or more dsRNA binding proteins (dsRBP). Numerous dsRBPs are known to bind dsRNAs with high affinity to prevent degradation, bind and stabilize miRNA precursors, and to play an important role in siRNA and miRNA guided gene silencing. It is proposed that expression of a dsRBP will enhance the stability and increase the concentration of available therapeutic nucleic acids by limiting their degradation, increasing the concentration of miRNA precursors and therefore their mature products, and providing necessary components for participation in targeted gene silencing. In an advantageous embodiment the dsRBP is TAR RNA-binding Protein (TRBP). Additionally, this platform has the capability to encode/deliver a wide range of other NA molecules, including siRNAs/shRNAs, miRNA mimics and inhibitors. Other possible dsRNA binding proteins include Nuclear factor 90, (NF90), ZNF346, SiD-1 and Ku70 (and combinations thereof).

In a second aspect the present invention provides a nonpathogenic bacterium or yeast comprising a prokaryotic or eukaryotic vector, where the vector includes a DNA molecule encoding one or more NA molecules, including for example short double stranded RNAs (e.g. siRNAs/shRNAs), and a promoter to control transcription of the short double stranded RNAs, wherein the short double stranded RNAs interfere with one or more target RNA molecules and wherein the bacterium is engineered to be deficient in RNase activity. In an advantageous embodiment the bacterium lacks a functional rnr gene. In addition to RNase R knockout, other RNase proteins that can be targeted for knockout include RNase E, RNase I, RNase H, RNase J and combinations thereof.

In a third aspect the present invention provides a nonpathogenic bacterium comprising a prokaryotic vector, where the vector includes a DNA molecule encoding one or more NA molecules, including for example short double stranded RNAs (e.g. siRNAs/shRNAs) and a promoter to control transcription of the short double stranded RNAs, wherein the short double stranded RNAs interfere with one or more target RNA molecules and wherein the bacterium is engineered to methylate the 3' terminal nucleotide of siRNA. More specifically, the bacterial system expresses a methyltransferase gene, including HEN1 or another methyltransferase gene with 2'-O-methyltransferase activities, whereby the methyltransferase promotes the methylation the 3' terminal nucleotide of siRNA. Methylation of the 3' terminal nucleotide provides protection against the predominant sources of RNA degradation including 3'-5' degradation and 3' uridylation, ultimately serving to enhance the stability and/or increase the concentration of therapeutic NAs available for participation in RNAi pathways.

In a fourth aspect the present invention provides a nonpathogenic bacterium or yeast comprising a prokaryotic or eukaryotic vector wherein the vector includes a DNA molecule encoding one or more NA molecules, including for example short double stranded RNAs (e.g. siRNAs/shRNAs), and a promoter to control transcription of the short double stranded RNAs, wherein the short double stranded RNAs interfere with one or more target NA molecules and wherein the bacterium is engineered to express a dsRNA binding protein (dsRBP) and a HEN1 gene. In an advantageous embodiment the *E. coli* bacterium of the fourth aspect is engineered to be deficient in RNase activity. In a particularly advantageous embodiment the bacterium lacks a functional rnr gene.

In a fifth aspect the present invention provides a nonpathogenic bacterium or nonpathogenic yeast comprising a prokaryotic or eukaryotic vector, said vector comprising a DNA molecule encoding one or more nucleic acids and a prokaryotic promoter to control transcription of the therapeutic nucleic acids, wherein the nonpathogenic bacterium or yeast is engineered to exhibit a reduced nucleic acid degradation phenotype.

In a broad sense the one or more nucleic acids interact with one or more molecules or compounds. This could be for the purpose of up-regulating or down-regulating an effect in a target cell or organism, such as for treating the organism for a disease condition or for studying the effect of a gene or gene product in an organism. In an advantageous embodiment the one or more nucleic acids is a therapeutic nucleic acid. The therapeutic nucleic acid can interfere with one or more targets, such as a pathogen nucleic acid sequence. A therapeutic NA (TNA), could interfere with many types of target molecules (RNA, DNA, other oligonucleotide, etc.) depending on the nature and identity of the therapeutic nucleic acid. A TNA could interact (e.g. interfere, target, modify, alter) with one or more host factors or pathogen factors, where the host factor could be an oligonucleotide, protein, gene, etc. By way of example, the TNA could interact with a cancer gene or the product of a cancer gene to regulate the cancer or study the cancer or a cancer therapy. In a further advantageous embodiment the reduced nucleic acid degradation phenotype increases the stability, magnitude and/or duration of the intended therapeutic effect or activity. It is contemplated that the nonpathogenic yeast would employ an appropriate eukaryotic plasmid/episome and promotor sequence.

In a sixth aspect the present invention provides a nonpathogenic bacterium or nonpathogenic yeast comprising a prokaryotic or eukaryotic vector, said vector comprising a DNA molecule encoding one or more nucleic acids and a prokaryotic or eukaryotic promoter to control transcription of the therapeutic nucleic acids, wherein the nonpathogenic bacterium or yeast is engineered to have a chromosomal integration of the inv, hlyA, HEN1, TRBP, and/or HA-1 genes. The chromosomal integration of inv, hlyA, HEN1, TRBP, and/or HA-1 genes provides a way to enhance the expression of these genes (more stable and greater expression if expressed from bacteria's genome vs plasmid) and improves the stability of the delivery system. It produces a system that is easier for bacteria to express from the genome relative to one where the bacteria must maintain a plasmid and express the gene from the plasmid. In other words, it is more stable and results in greater expression if expressed from bacteria's genome rather than the plasmid. It is contemplated that the nonpathogenic yeast would employ an appropriate eukaryotic plasmid/episome and promotor sequence.

BRIEF DESCRIPTION OF THE DRAWINGS

For a fuller understanding of the invention, reference should be made to the following detailed description, taken in connection with the accompanying drawings, in which.

Figure 1:
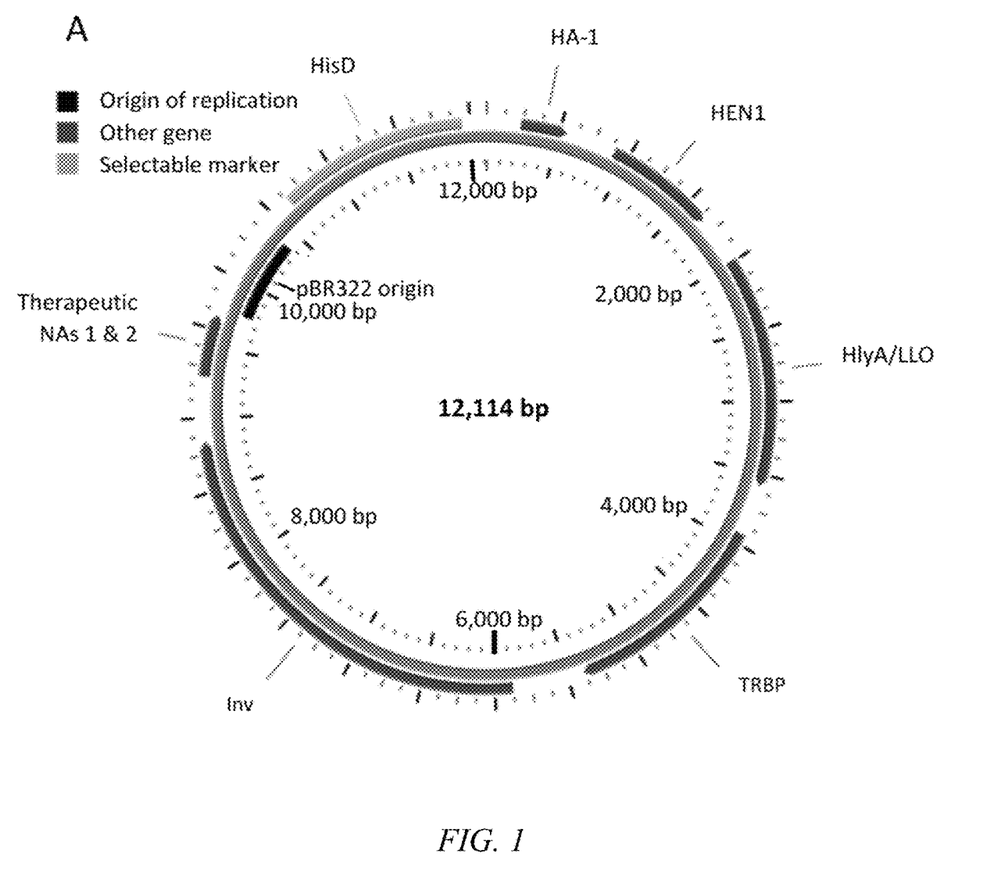
FIG. 1 is a diagrammatic representation of two versions of therapeutic NA generating plasmids. (A) The plasmid version A contains all genes necessary for targeting and delivery in addition to enhancers of therapeutic NA stability and is very large and unstable at over 12,100 bp. (B) The plasmid version B contains only the therapeutic NA sequences and the HisD antibiotic-free selection marker as all other necessary genes have been transferred to the delivery vehicle chromosome for improved efficiency and stability and a small plasmid size of approximately 4,700 bp.
Figure 2:
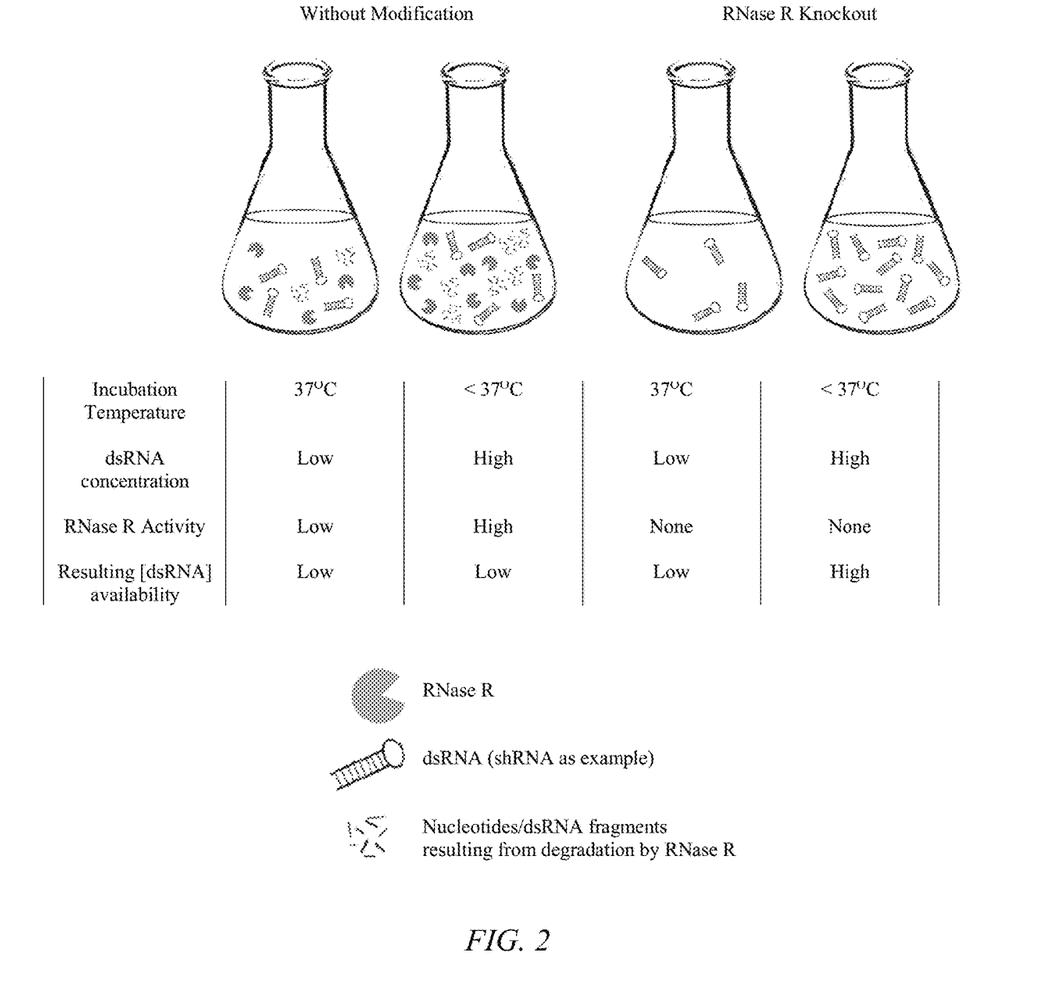
FIG. 2 is a drawing depicting the elimination of RNase R activity. Eliminating RNase R function in the delivery vehicle means that this heat-shock protein is not induced at low incubation temperatures. Since NAs have greater stability at lower temperature, incubating at 17° C. for example in the absence of RNase R yields a higher concentration of therapeutic NAs for delivery to sites of disease.
Figure 3:
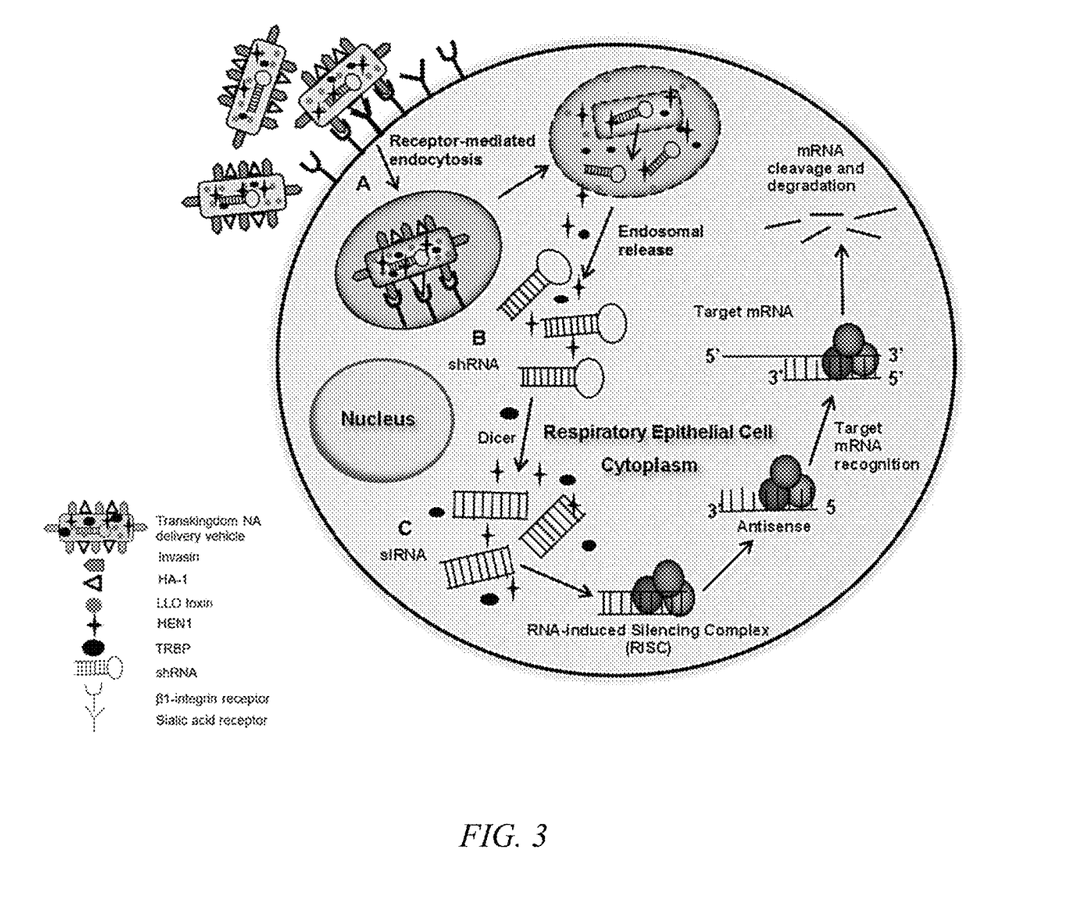
FIG. 3 is diagrammatic representation of the transkingdom nucleic acid delivery vehicles' mechanism of action in a respiratory epithelial cell, with the enhancements taught herein.
Figure 4:
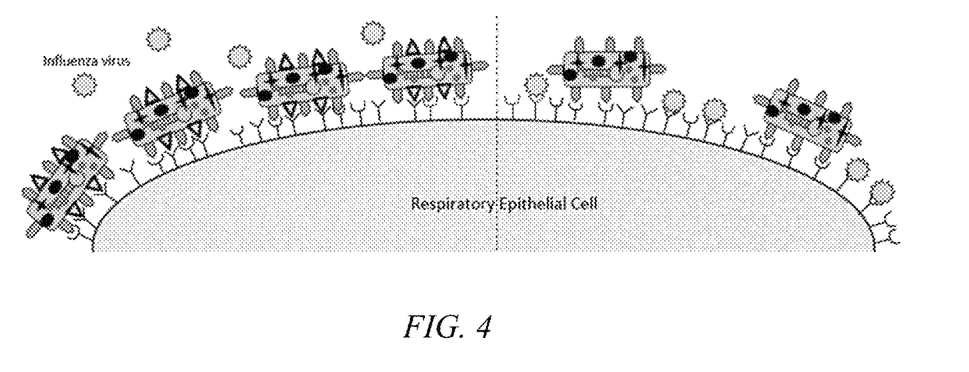
FIG. 4 is a drawing depicting the enhanced delivery vehicle (depicted to the left) that expresses cell surface proteins invasin and HA-1 which bind β1 integrin and sialic acid receptors, respectively, for specific delivery to sites relevant to disease. This allows for greater invasive properties compared to the current state of the art which only expresses invasin protein (depicted to the right). The enhanced delivery vehicles are also able to compete with pathogens that bind the same host cell surface receptors, thereby reducing pathogen uptake.

FIG. 5 is a drawing depicting the delivery vehicle expression of a dsRBP, such as TRBP, which binds to dsRNA and stabilizes it through processing by Dicer to produce siRNAs which are subsequently loaded into the RISC complex for guide strand recognition and interaction with the target sequences. shRNAs (and other dsRNA nucleic acids) unbound by TRBP are vulnerable to degradation by RNases. A greater availability and abundance of TRBP correlates with greater shRNA stability and a higher concentration of guide strand siRNA sequences.

FIG. 6 is a drawing and associated histogram. (Top Drawing) The enhanced delivery vehicle expresses a 3' methyltransferase such as HEN1 which methylates the 3' terminal nucleotide of the forward and reverse strands of siRNA, thereby providing protection from RNases which would normally cause degradation beginning at the 3' terminal nucleotide. The 3' methyl groups also prevent uridylation which is known to contribute to RNA degradation. (Bottom Graph) After generation and delivery by the enhanced delivery vehicle expressing HEN1, the graph depicts copies of methylated siRNA (me-siRNA) expected per ng cDNA when compared to un-methylated siRNA (siRNA), over time.

DETAILED DESCRIPTION OF THE PREFERRED EMBODIMENT

This invention advances the delivery of therapeutic nucleic acids by providing a versatile delivery platform that can be tailored to target specific tissues for a wide range of therapeutic applications in a variety of different eukaryotic species. Therapeutic nucleic acids initially showed enormous potential for the treatment of disease, but that potential has not been fully realized due to shortcomings in the delivery of those nucleic acids to target tissues and cells. Significant improvements can be made to the magnitude and duration of silencing effect and to the use of delivery platforms to target numerous relevant tissues for the future development of a wide range of clinical applications. In a more focused sense, improvements can be made to have enhanced stability of both the delivery vehicle and the nucleic acids generated by the delivery vehicle, improved invasive properties of the vehicle, improved safety, and improved properties for manufacturing processes and regulatory consideration.

Exosomes, liposomes and other lipid vesicles have been used as NA delivery platforms to carry RNA payloads for delivery to distant tissues. Delivery vehicles such as liposomes have drawbacks including leakage of vesicle content, batch-to-batch variation, high cost of production, and limited targeting ability. This transkingdom delivery system is based on the use of a non-pathogenic bacterial-mediated RNAi delivery vehicle that uses natural receptor-mediated endocytosis for specific intracellular delivery at the tissue site of action, resulting in the accumulation of shRNAs in endosomes and the efficient release of the shRNA payload into the target cell's cytoplasm for RNAi silencing. These transkingdom vehicles have been *Escherichia coli* (*E. coli*) cells that have been engineered to specifically target mucosal epithelial tissues and deliver a payload of constitutively generated shRNAs in a sequence-independent manner.

Transkingdom RNA interference using an engineered RNAi delivery platform employing nonpathogenic bacteria containing an shRNA expression plasmid has been used to dramatically reduce the severity of AIV infection and inhibit AIV shedding in avian epithelial cells. (Linke, Lyndsey M. et al. "Inhibiting Avian Influenza Virus Shedding Using a Novel RNAi Antiviral Vector Technology: Proof of Concept in an Avian Cell Model." *AMB Express* 6 (2016): 16. *PMC*. Web. 27 Mar. 2018.) Transkingdom RNA systems for the delivery of shRNAs are taught in US 2016/0177296 A1 to Linke et al., the contents of which are incorporated by reference in their entirety. Transkingdom nucleic acid delivery systems use nonpathogenic bacteria, such as *E. coli*, engineered to transcribe shRNA from a plasmid. Transkingdom nucleic acid interference was rendered relevant for clinical applications by including additional genes on the shRNA expression plasmid that facilitated both the entry of the bacteria into the target cell and the subsequent release of the contents of the nonpathogenic bacteria following its entry into the target cell. Specifically, systems were developed that encode two factors, or genes, allowing shRNA delivery to mucosal epithelial cells; the invasin gene (Inv) and the listeriolysin O gene (hylA). The Inv gene is necessary for expression of invasin protein on the *E. coli* surface (Xiang et al. 2006), which interacts with β(1) integrin receptors present on mucosal epithelial cells resulting in receptor mediated endocytosis (Conte et al. 1994; Isberg and Barnes 2001; Isberg and Leong 1990). The hlyA gene encodes a pore-forming toxin, Listerolysin O (LLO), that facilitates the rupture of the endosomal membrane and the subsequent release of shRNA into the cell's cytoplasm (Grillot-Courvalin et al. 1998; Mathew et al. 2003; Nguyen and Fruehauf 2009; Radford et al. 2002; Xiang et al. 2006). The transkingdom nucleic acid delivery vehicle used in the studies above was a diaminopimelic acid (Dap) auxotrophic mutant and was kanamycin resistant.
Figure 5:
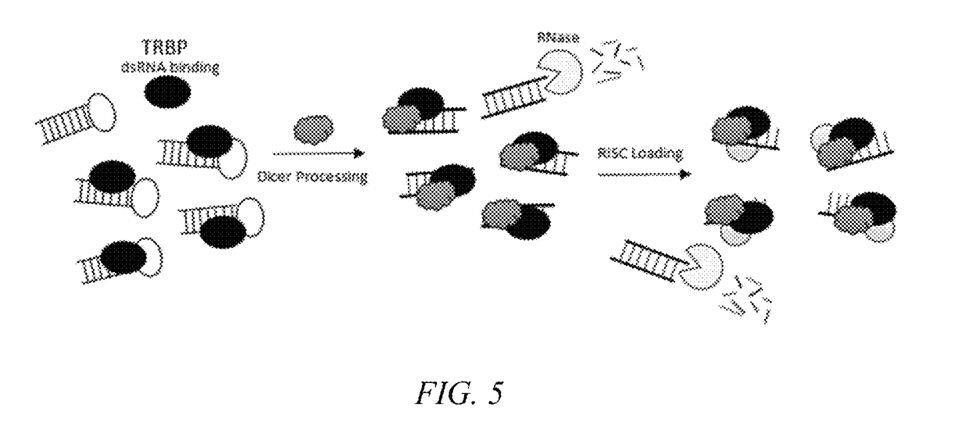
Figure 6:
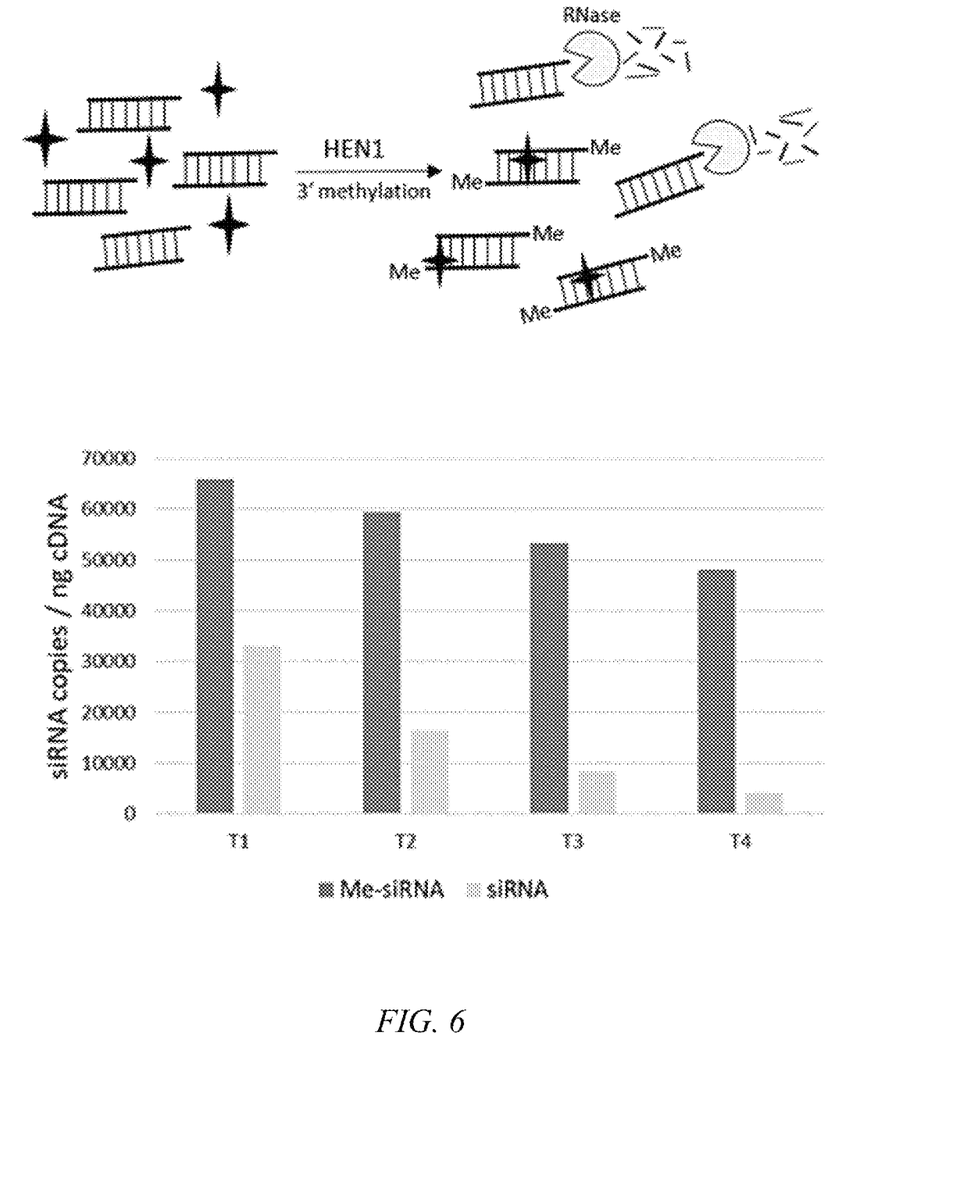

These vehicles express Listerolysin O (LLO), a pore-forming toxin that allows the *E. coli* to escape the host endosome for release in the cytosol. The lack of nutrients inside the endosome facilitates bacterial lysis and the release of the LLO toxin which breaks down the endosomal membrane. The released shRNA are then processed into siRNA, and incorporated into the RNA-induced Silencing Complex (RISC).

These bacteria can regulate the delivery of shRNA. Once inside the host endosome, they become non-viable and no longer generate shRNA, eliminating the potential to overload the RISC mechanism and cause unwanted side effects to the host.

Transkingdom delivery vehicles can be transformed with a shRNA (or other therapeutic nucleic acid) expression cassette under the control of a prokaryotic RNA polymerase, such as the T7 polymerase, which can constitutively generate shRNA (or other therapeutic nucleic acid) under the control of the prokaryotic RNA polymerase against any clinical target gene of interest. Inclusion of a prokaryotic RNA polymerase implicates the bacterium as the source of expression of the desired product (e.g. the therapeutic nucleic acid) rather than the target cell. In the case of viral targeting, this platform technology could encode several shRNAs to target multiple viral RNA targets. In addition, other therapeutic nucleic acids can be included in place of, or in addition to, sequences producing shRNA in the expression cassette and the system could target additional pathogens or disease-associated molecules. This cocktail approach would limit the risk for viral escape by mutation. Additionally, this platform has the capability to encode a wide range of other NA molecules, including miRNA mimics and inhibitors. In other words, the proposed system has the capability to deliver other nucleic acids, in addition to siRNA/shRNA and is a significant improvement over the current state of art, which has not been adapted for the delivery of molecules such as micro RNA mimics or micro RNA inhibitor encoding and delivery.

The transkingdom delivery platform uses non-pathogenic bacteria that are diaminopimelic acid (Dap) auxotrophic. Certain bacteria, including *E. coli*, require Dap as a component of their cell wall and auxotrophs are unable to proliferate or survive outside of a Dap-supplemented medium. As non-pathogenic and non-colonizing bacteria, these vehicles do not pose any known risk to the host and have a confirmed safety record. Moreover, as non-conjugative vectors, there is no risk of integration into the host genome and tumorigenesis. In previous work (data unpublished), we demonstrated that these bacterial vehicles were not associated with any observed clinical illness, toxicity, or tissue pathogenesis in the species tested; namely chickens. Hence, the bacteria are "non-pathogenic" to the host cells or the target species and do not cause disease.

We are proposing to improve the current transkingdom delivery vehicles with unique modifications, centered on improving the stability of the delivered nucleic acids (NAs), improving the resistance of the double-stranded interfering RNAs to cellular decay mechanisms, improving the invasive properties, and/or improving manufacturing processes, safety, and regulatory issues associated with the delivery system. The justification for increasing dsRNA stability is that stabilizing the payload of shRNAs (and other NA molecules that could be generated and delivered using this delivery platform) will increase shRNA availability and the processing of more siRNA. The justification for improving the invasive properties is that the transkingdom delivery vehicles will have a greater opportunity to attach to a wider range of host cells, thereby increasing the number of transkingdom delivery vehicles that are taken up and intracellularized. These improvements should provide a more robust and prolonged RNAi effect for optimal therapeutic applications. Taken individually or in any combination, these improvements advance the translational potential of the technology for therapeutic and clinical applications.

Improving the invasive properties and stability of the delivered NAs can be achieved through multiple approaches as taught herein. A first approach to improving the delivery vehicle is to include a dsRNA binding protein (dsRBP) that will increase the stability of dsRNAs. A second approach to improving the delivery vehicle is to eliminate activity of a key bacterial enzyme involved in RNA degradation. A third approach to improving the delivery vehicle is to include a gene/protein that will cause stabilizing methylation of the dsRNA. In one embodiment, the TAR RNA-binding Protein (TRBP) and the C-terminal methylase domain of the HEN1 gene would be encoded, and RNase R activity in the *E. coli* bacterial delivery vector would be knocked out. These formulation improvements will be utilized to deliver nucleic acids, including shRNA, to a wide range of mucosal epithelial tissues, including upper/lower respiratory, oral, gastrointestinal (GI), vaginal, rectal and ocular epithelium. The methods of administering these improved transkingdom NA delivery vehicles include intranasal dosing to nasal cavity for local action, aerosolization for upper and lower respiratory targeting, absorption in the oral cavity for buccal delivery, ingestion for GI adsorption, application to delicate genital mucosal epithelium, and topical administration for ocular delivery. These improved delivery vehicles could be used to prevent and/or treat a wide range of diseases (infectious, allergic, cancerous, and immunological) in a wide range of species (human, avian, swine, bovine, canine, equine, feline).

We propose to enhance targeting of the delivery vehicle to epithelial cells expressing sialic acid receptors by engineering the delivery vehicle to express the influenza virus hemagglutinin (HA-1) protein. It is contemplated that HA-1 could be expressed alone or in combination with the invasin protein in a delivery vehicle. Expression of HA-1 in the delivery vehicle would thereby not only provide an appropriate means for bacterial cell uptake and intracellularization into the host cell, but it would mechanically prevent the uptake and infection of competing pathogens (e.g. influenza virus and other pathogens using sialic acid receptors for attachment/entry) by blocking access to receptor sites on the target cell. In the case of viral and bacterial infections that target the gut, ocular, and respiratory mucosal epithelial cells, the inclusion of the HA-1 protein for vehicle delivery would provide a greater affinity for targeting those tissues for localized delivery and maximum protection against invading pathogens, therapeutically and prophylactically.

Example 1—Engineering *E. coli* to Express a dsRBP

In a first aspect, improving the delivery vehicle can be achieved by cloning a dsRNA binding protein domain into the therapeutic nucleic acid-generating plasmid for expression under the control of the prokaryotic RNA polymerase, or chromosomally expressing the dsRNA binding protein (dsRBP) on the *E. coli*, so that the inclusion of a dsRBP will increase the stability of dsRNAs produced by the non-pathogenic bacterium.

The family of dsRBPs comprises one or more evolutionarily conserved dsRNA-binding domains (dsRBDs) of 65-68 amino acids found in eukaryotes, prokaryotes, and viral-encoded products (Ryter et al 1998). These dsRBDs were first recognized in 1992 as being responsible for the many interactions between proteins and RNA duplexes (Johnston et al 1992; McCormack et al 1992). The dsRBP family includes the TAR RNA-binding Protein (TRBP), which exclusively interacts with dsRNA in a non-sequence-specific manner (Ryter et al; Manche et al). TRBP contains three highly conserved dsRBDs, however the first and second have high affinities for binding and preventing dsRNA degradation (Yamishita et al; Daviet et al; Tian et al). TRBP can participate in RNAi (Gatignol et al, Gredell et al, Lee and Ambros, Tian et al; Daniels et al; Parker et al). These two TRBP binding domains can be used to bind and prevent shRNA/siRNA degradation in vitro and in vivo, play a role in gene silencing induced by siRNAs and microRNAs (miRNAs), and play a physiological role in the cell by binding miRNA hairpin precursors and stabilizing their path to maturation (Chendrimada et al; Koh et al; Gregory et al; Dar et al; Yamashita et al; Koh et al). Accordingly, just the two domains could preferentially be used or all three could be included in a transkingdom vector. In summary, TRBP functions like a dsRNA gatekeeper. Simultaneously encoding this dsRNA binding protein in a transkingdom vector represents a formidable approach to improving the transkingdom NA delivery vehicles. Other dsRBPs that could be considered for expression instead of or in addition to TRBP include nuclear factor 90, (NF90), ZNF346, SiD-1 and Ku70 (and combinations thereof).

Example 2—RNase R Knockout

In a second aspect, improving the properties of the delivery vehicle can be achieved by eliminating or reducing the activity of the enzyme responsible for RNA degradation. In bacteria such as E. coli, structured RNA duplex decay is exclusively carried out by RNase R, a hydrolytic 3' to 5' exoribonuclease (Matos 2009; Khemici and Carpousis; Cheng and Deutscher 2005; Vincent and Deutscher 2009; Awano et al 2007, Awano 2010; Chen et al 1998; Hossain 2015; Hossain 2016). As is the case with shRNA/siRNA molecules, RNase R is able to degrade these dsRNAs by specifically binding the 3' single-stranded overhangs (Cheng and Deutscher, Vincent and Deutscher 2006). In fact, RNase R is the only 3' to 5' exoribonuclease capable of chewing through extensive secondary RNA structures (Vincent and Deutscher 2009). RNase R is a cold-shock protein encoded by the rnr gene and its activity can be modulated by altering the growth conditions of the bacterial cell (Chen et al 1998; Cheng and Deutscher; Cairrao and Arraiano 2006; Cairrao et al 2003). When the exponential growing temperatures for E. coli shift from 37° C. to 15° C., the RNase R cold shock response is stimulated (Awano et al 2007). Meaning, RNase R activity increases and results in greater dsRNA decay. Studies have demonstrated that the RNase R helicase activity plays a necessary catalytic role for effective nuclease activity against dsRNA, especially at lower incubation temperatures when there is coincidently a greater concentration of more stable dsRNA substrates (Hossain et al 2015, Hossain et al 2016, Awano et al 2007; Awano et al 2010). E. coli mutants lacking the rnr gene were able to replicate efficiently at standard 37° C. growing temperatures, but were unable to digest dsRNA (Chen et al 1998; Khemici and Carpousis; Cheng and Deutscher; Vincent and Deutscher 2009; Vincent and Deutscher 2006; Awano et al 2007; Hossain et al 2015; Hossain et al 2016 (both); Awano et al 2010). The stability of shRNA and siRNA molecules is improved at lower temperatures so dropping the culture temperature would be favorable for maintaining high NA concentrations, but only if the cold shock induction of RNase R activity could be avoided. Therefore, knockout of RNase R activity in the E. coli bacterial delivery vehicle can lead to enhanced delivery of NAs. In a modified E. coli bacterial delivery vehicle with RNase R knockout, following bacterial cell exponential growth when shRNA generation is maximized, halting bacterial growth and incubating the cultures below 37° C. will inhibit dsRNA decay, thereby enhancing the stability of the encoded therapeutic shRNAs. It is therefore contemplated that the transkingdom system can comprise a non-pathogenic bacterium, such as E. coli, deficient in the rnr gene that have been transformed with a special shRNA (or other therapeutic nucleic acid) generating plasmid. It is further contemplated that these rnr-deficient E. coli bacteria can be propagated at a reduced temperature (i.e. below 37° C.), such as 33° C. or lower, 30° C. or lower, 27° C. or lower, 25° C. or lower, 22° C. or lower, 20° C. or lower, 17° C. or lower, preferably 25° C. or lower, most preferably 17° C. or lower. Propagation at such a reduced temperature will allow for production of the desired shRNA, while limiting their degradation. It is further contemplated that the shRNA generating plasmid used in the rnr-deficient transkingdom nucleic acid delivery system can include a gene encoding a dsRBD, such as TRBP. One approach to knockout can occur by recombineering the deletion so the E. coli no longer makes RNase R protein, essentially creating an E. coli mutant. Other approaches to eliminating rnr gene functionality include Cre-lox, FLP-FRT, selection-counterselection, and CRISPR/Cas mediated gene editing. Knockout is contemplated to be directed not just to the rnr gene, as there are other genes that could be knocked out to eliminate RNase activities in E. coli. In general, elimination of RNase catalytic activity, including elimination of RNase R, in the E. coli can enhance efficacy. Other targets for knockout can include, but are not limited to, RNase E, RNase I, RNase H, RNase J, and combinations thereof.

Example 3—Methylation of the 3' Terminal Nucleotide of the siRNA

In a third aspect, improving the properties of the delivery vehicle can be accomplished by including a gene, such as on a therapeutic NA generating plasmid, that will cause stabilizing methylation of the shRNA. As discussed above, degradation of dsRNA is predominately caused by exonucleases (Czauderna, et al. 2003). Methylation of the 3' terminal nucleotide of siRNA can provide stabilizing effects against exonucleases, as it protects from 3'-5' degradation and 3' uridylation of siRNA (Ji & Chen 2012; Lifang, et al. 2010; Kurth & Mochizuki 2009; Chan, et al. 2009). RNAi activity is maintained when siRNA molecules are modified only at the terminus of the sense strand, or in the case of siRNA hairpins, the 3'-terminus (Czauderna, et al. 2003). Methylation of the 3'-terminus is required for functionality of all plant siRNAs and is observed in some mammalian and bacterial siRNAs as well. The HEN1 gene encodes the methyltransferase Hen1, a methylase that catalyzes the S-adenosylmethionine-dependent transfer of a methyl group to the 2'-hydroxyl of the 3'-terminal nucleotide (Jain & Shuman 2010; Baranauske, et al. 2015). The Hen1 domain of several bacterial species has been proven functionally equivalent to their eukaryotic homologs (Chan, et al. 2009). Using methylation assays, Chan, et al. (2009) showed that human and bacterial (*Clostridium thermocellum*) recombinant Hen1 proteins exhibit enzymatically equivalent methylation activity on small single-stranded RNAs (21-30 nt). However, the C-terminal methylase domain of the *C. thermocellum* Hen1 showed improved enzymatic activity over its full-length counterpart and the human Hen1, demonstrating that this domain is able to function independently. Therefore, packaging the HEN1 gene, or in an advantageous embodiment packaging the C-terminal methylase domain of the HEN1 gene, in the transkingdom delivery vehicle will provide stabilizing effects for the siRNA against exonucleases. In other words, HEN1 will actively methylate and enhance the stability of the encoded shRNAs, thereby providing shRNAs optimally suited for therapeutic applications in vivo.

Example 4—Non-Pathogenic Bacteria Engineered to Express Influenza Hemagglutinin-1 (HA-1) Protein In a fourth aspect, improving the localized and targeted delivery of the delivery vehicle to mucosal tissues, specifically respiratory mucosal tissues, could be achieved by engineering the bacterium to express the influenza hemagglutinin-1 (HA-1) protein either via genomic (chromosomal) or plasmid expression. HA-1 is a glycoprotein found on the surface of influenza viruses and facilitates viral attachment and entry into target cells by receptor mediated endocytosis (White et al. 1997). HA-1 represents the globular head which contains a receptor site that has high affinity for sialic acid, present on the surface of target cells, including respiratory mucosal epithelial cells (Russell et al 2008). In a preferred embodiment, HA-1 is expressed on the *E. coli* surface and interacts with sialic acid surface receptors on mucosal epithelial cells for bacterial uptake. The HA-1 protein could be derived from any influenza type A or B virus subtype. The full length HA-1 gene is cloned into the shRNA generating plasmid (or other plasmid constructed to generate therapeutic nucleic acids) using standard cloning methodologies, or integrated into the *E. coli* chromosome using, for example, the Gibson assembly method and a commercially available Gibson Assembly Cloning kit, the flippase/flippase recognition target (FLP/FRT) site-directed recombination technology (Pósfai et al 1994, Bertram et al 2009), selection-counter-selection strategies, or CRISPR/Cas manipulation (Jiang et al 2013, Jiang et al 2015, Pyne et al 2015, Reisch et al 2015, Zhao et al 2016).

The addition of HA-1 protein on the surface on the *E. coli* cells is an improvement over the single expression of Inv alone. In one embodiment, HA-1 would be expressed independently or in a separate embodiment, expressed in combination with Inv to provide a unique facet that would not be offered by Inv alone. In the case of viral and bacterial pathogens that utilize sialic acid receptors for intracellular entry into target cells, for example influenza viruses infecting respiratory tissues, the binding of the *E. coli* cells via the HA-1 protein would physically block the essential binding interaction between an infecting pathogen (i.e. influenza virus) with sialic acid receptors on target cells. This would thereby not only provide an appropriate means for bacterial cell uptake and intracellularization into the host cell, but it would mechanically prevent the uptake and infection of competing pathogens (i.e. influenza virus). In the case of viral and bacterial infections that target the respiratory mucosal epithelial cells, the inclusion of the HA-1 protein for vehicle delivery would provide a greater affinity for targeting those tissues for localized delivery and maximum protection against invading pathogens, therapeutically and prophylactically. Other pathogens including coronaviruses, norovirus, rotavirus, mumps virus, parainfluenza, *Clostridium botulinum*, and *Vibrio cholerae* (Mastrovich et al. 2013; Varki 2008) are known to produce proteins that bind to sialic acids on host cells to facilitate entry or infection. It is further contemplated that those proteins, or binding protein domains from those pathogen's proteins, could be used as an alternative to the influenza HA-1 protein (or the sialic acid residue binding domain from HA-1).

Example 5—Removal of Antibiotic Resistance Gene from the Non-Pathogenic Bacterium In a fifth aspect, the manufacturing process, safety, and regulatory consideration of the delivery system are improved by removing an antibiotic resistance gene, including but not limited to kanamycin resistance (potentially included on the plasmid as a selection marker). Antibiotic resistance genes are included as selection markers on the majority of bacterial expression vectors (Peubez, et al. 2010). Antibiotic resistance is a major concern for human and animal health and the regulatory requirements for biological agents are becoming more stringent to reflect this (Mignon 2015). Eliminating the need to include an antibiotic in the manufacturing process reduces costs and eliminates concerns that antibiotic resistance in an unintended host could be induced by a bacterial delivery system. In an advantageous embodiment, this delivery vehicle uses an antibiotic-free system, such as the amino acid auxotrophy and complementation system described in example 6 below, to specifically select for the desired plasmid-containing bacteria.

Example 6—Creation of a Nonpathogenic Auxotrophic Mutant

The functionality and stability of the delivery system are improved by inclusion of a metabolic or nutritional selection marker, including but not limited to amino acid auxotrophy and complementation, thus improving the manufacturing process, safety, and regulatory consideration of the delivery system.

In a sixth aspect, the functionality and stability of the delivery system are improved by inclusion of a metabolic or nutritional selection marker, including but not limited to amino acid auxotrophy and complementation (e.g. targeting essential amino acids including but not limited to histidine). One or more critical genes in an amino acid synthesis pathway can be targeted on the *E. coli* chromosome to create an auxotrophic mutant unable to produce the required amino acid. Supplementation of the knocked-out gene or genes on the plasmid would permit the survival of only the *E. coli* containing the plasmid, allowing for efficient and reliable selection in culture medium lacking the amino acid (Peubez, et al. 2010; Mignon, et al. 2105; Fiedler, et al. 2017). A similar principle holds for other nutrients or nutrient processing pathways critical for bacterium survival. This approach facilitates antibiotic-free manufacturing which further supports the improvements described in example 5, above. In *E. coli* for example, histidine is synthesized in a ten-step pathway wherein the hisD gene product, the bifunctional enzyme histidinol dehydrogenase, catalyzes the final two oxidation steps (Ramage, et al. 2012; Matte, et al. 2003) and the hisB product, the bifunctional enzyme histidinol phosphatase, catalyzes the seventh and ninth steps (Winkler & Ramos-Montanez 2009; Chiariotti, et al. 1986). The hisA, hisB, hisC, hisD, hisE, hisG, hisH, and hisI gene products are required for histidine synthesis and therefore *E. coli* growth on minimal medium (Joyce, et al. 2006), however, computational models and published experiments indicate that hisD or hisB knockout produces a strain with growth fully dependent on the presence or absence of histidine and independent of other amino acids or metabolites present in the culture medium (Bertels, et al. 2012; Tepper & Shlomi 2011).

In an advantageous embodiment, the *E. coli* are engineered as histidine auxotrophs wherein the bacteria lack a functional hisD gene (product: histidinol dehydrogenase) and the shRNA generating plasmid (or other plasmid constructed to generate therapeutic NAs) is engineered to express the hisD gene, thereby supplementing the histidine biosynthetic pathway and permitting bacterial replication in a histidine-deficient medium. In another embodiment, the *E. coli* are engineered to lack a functional hisA, hisB, hisC, hisE, hisG, or hisH gene and the prokaryotic vector is engineered to express the missing his gene. In the case of a gene involved in histidine synthesis, the gene may be expressed on the plasmid under the control of the bacterial hisp1 promoter or another prokaryotic promoter (Alifano, et al. 1996).

Example 7—Expression of Multiple Therapeutic Nucleic Acids by a Transkingdom Delivery Vehicle In a seventh aspect, the functionality and stability of the delivery system are improved by enabling expression of individual or multiple therapeutic NAs on a single plasmid. Many different configurations are possible including 1) NAs expressed in a single expression cassette in tandem under the control of a single promoter, 2) NAs in independent expression cassettes each under the control of its own promoter and terminator but with competitive expression due to use of the same promoter sequence, and 3) NAs in independent expression cassettes each under the control of a different promoter for differential expression. As demonstrated in numerous published studies, specific details of the plasmid configuration, including spacer lengths and sequences, promoter sequences and strengths, therapeutic NA type (e.g. shRNA) and size, and the number of therapeutic NAs being expressed all affect NA expression levels, siRNA folding/processing, silencing specificity, and RNAi activity. While much of this work has been done for an HIV model, good methods are available to guide plasmid design and optimization appropriately with each approach (Liu, et al. 2007; Mcintyre, et al. 2011; Spanavello, et al. 2016; Choi, et al. 2015; Wang, et al. 2013). Expression of multiple NAs on a single plasmid achieves several important improvements: classification as a single 'active' ingredient for certain regulatory agencies rather than each NA-expressing plasmid within an *E. coli* bacterium being viewed as separate, simplified manufacturing by only having to culture a single stock of *E. coli* containing all relevant NA targets, and expanded targeting capabilities to reduce risk of pathogen mutation and permit treatment of multiple diseases with a single therapy.

Tandem expression of multiple specific nucleic acid sequences on the plasmid provides a system that is easier to and less expensive to manufacture (e.g. it can be manufactured as single culture) even if expressing multiple nucleic acids with different targets. This improves the stability of the system by reducing variability and making the manufacturing processes more predictable. This also facilitates a simplified regulatory pathway (US and international) as a single active/therapeutic instead of multiple, thereby reducing cost and resource requirements.

Example 8—Chromosomal Expression of Inv, LLO, HA-1, HEN1, and/or TRBP

In an eighth aspect, the stability of Inv, LLO, HA-1, HEN1, and/or TRBP expression, the expression (overall abundance) of Inv, LLO, HA-1, HEN1, and/or TRBP, and the manufacturing process of the delivery vehicle, are improved by integrating the expression of each of these genes onto the *E. coli* chromosome (or other nonpathogenic bacterium or yeast). This produces a strain of bacteria that stably express the Inv, LLO, HA-1, HEN1, and/or TRBP gene. In constructing the strain, regions along the bacterial chromosome where the expression cassettes will be integrated into the engineered bacterium can be located. The full-length sequence, or a shortened portion thereof, of any combination of these genes (Inv, LLO, HA-1, HEN1, and/or TRBP) can be integrated into the *E. coli* chromosome using, for example, the Gibson assembly method and a commercially available Gibson Assembly Cloning kit, the flippase/flippase recognition target (FLP/FRT) site-directed recombination technology (Pósfai et al 1994, Bertram et al 2009), selection-counter-selection strategies, or CRISPR/Cas manipulation (Jiang AEM, Jiang NBT 2013, Pyne AEM, Reisch et al 2015, Zhao et al 2016). Genomic expression is an improved approach to plasmid expression for several reasons. Plasmid carriage and maintenance puts the *E. coli* cells at a selective disadvantage. Reliance on expression from the plasmid requires that the *E. coli* cells be grown under specific environmental conditions to maintain plasmid presence inside the bacteria. This complicates manufacturing and can result in greater bacterial stress. During manufacturing, variable conditions in large-scale fermentations influence the replication of the plasmid DNA in *E. coli* cells, thus affecting the efficiency (stability and abundance) of gene expression significantly. In this embodiment, genomic integration of these functional genes eliminates the bacterium's need to maintain plasmid replication, especially when growing conditions are variable. Additionally, the *E. coli* cells will grow faster if these genes are eliminated from the plasmid and integrated into the *E. coli* chromosome for expression (G Wegrzyn and A Wegrzyn 2002). In this embodiment, the genomic expression of Inv, LLO, HA-1, HEN1, and/or TRBP from the *E. coli* chromosome will also result in greater abundance of these genes compared to plasmid expression. Reliance on plasmid expression means the plasmids must replicate often enough to produce their copies in sufficient amounts for distribution to both daughter cells after division of a mother cell. This results in lower expression (lower abundance) of plasmid-derived genes in progeny cells compared to stable and consistent genomic derived expression. Overall, integration of Inv, LLO, HA-1, HEN1, and/or TRBP into the *E. coli* chromosome improves the stability and increases the expression of these genes, especially for large-scale manufacturing processes.

In one embodiment of the above methods of the invention, the bacterium is non-pathogenic or non-virulent. In another aspect of this embodiment, the bacterium is therapeutic. In another aspect of this embodiment the bacteria are invasive or have been engineered to be invasive and enter a host cell. Examples of such bacteria include *Listeria, Yersinia, Rickettsia, Shigella, E. coli, Salmonella, Legionella, Chlamydia, Brucella, Neisseria, Burkolderia, Bordetella, Borrelia, Coxiella, Mycobacterium, Helicobacter, Staphylococcus,*

*Streptococcus, Porphyromonas, Vibrio, Treponema, Lactobacillus*, and *Bifidobacteriae*. In another aspect of this embodiment, the delivery vehicle is a fungus cell such as *Saccharomyces* and *Candida* yeasts.

In an advantageous embodiment of the invention, the invasive delivery vehicles, containing the NA molecules, are introduced into a host by intravenous, intramuscular, intradermal, intraperitoneally, peroral, intranasal, intraocular, intrarectal, intravaginal, intraosseous, oral, immersion, topical, intraurethral, and aerosolization inoculation routes.

In an advantageous embodiment, this invention relates to a transkingdom platform for targeted intracellular delivery of RNAi mediating agents and other nucleic acids. Examples of such RNAi agents and NAs include, but not limited to, deoxyribonuclease (DNA), RNA, siRNA/shRNA, miRNA, antagomiRs, aptamers, mRNA, splice-switching oligonucleotides, defective interfering particles, and antisense oligonucleotides.

Routes of Pathogen Entry Across the Mucosa:

The surfaces where pathogens are most likely to invade the human body, including the pleura, peritoneum, and skin, are protected by the mucosal immune system (Janeway et al. 2001). Mucosal surfaces are the first line of defense to the inside of the body from pathogens, and allergens in the outside environment. Epithelial cells form tight junctions to create a dynamic layer in all mucosal surfaces (Parham 2014; Presland & Jurevic 2002). The moist mucus layer covering mucosal surfaces contains a mixture of 'defensive compounds' secreted by epithelial cells and leukocytes, which create a physical barrier, but may also directly act on select microbes (Linden et al. 2008). The respiratory tract, gastrointestinal tract, urogenital tract, and other organs such as the eyes, represent major systems containing mucosal epithelial surfaces (Parham 2014). The gastrointensinal (GI) tract alone has an impressive surface area of more than 400 square meters (Guandalini et al. 2008). When pathogens or allergens are successful in breaching mucosal defenses, disease response is typically contained to that compartment of the body (Janeway et al. 2001).

Exemplary Viruses that can be Targeted by the Proposed Transkingdom NA Delivery System:

Numerous diseases affect multiple tissue types containing mucosal epithelia. Herpes simplex virus types 1 and 2 (HSV-1 and HSV-2) replicate in mucosal epithelial cells including those of the mouth, eyes, and genitals (Chentoufi & BenMohamed 2012; Karasneh & Shukla 2011; NIAID). In the United States, around 65% of people are seropositive for HSV-1, while global prevalence is thought to be much higher with approximately 90% of people being infected with HSV-1 and/or HSV-2 (Wald & Corey 2007). In the developed world, HSV-1 is the leading cause of corneal blindness and viral encephalitis (Chentoufi & BenMohamed 2012). Perinatal transmission of HSV-2 in the birth canal is responsible for approximately 85% of neonatal herpes cases (Chentoufi & BenMohamed 2012). Influenza is a globally significant and highly contagious virus that infects respiratory tissues including the mucosa of the eyes, nose, lungs, and throat. Despite the availability of vaccinations, millions of people fall ill with seasonal influenza each year, and emerging and pandemic strains of the virus remain a threat (NIAID). Human papillomavirus (HPV) can infect the mucosal epithelial cells of the mouth, throat, and upper respiratory tract (Nguyen et al 2014; Rautava & Syrjanen 2011). HPV additionally infects anogenital epithelial mucosa and is one of the most common sexually transmitted disease globally, with an estimated 1-5.5 million new cases emerging annually in the United States alone (Burd 2003; MAID).

Other significant diseases affecting mucosal epithelial cells of the respiratory system include leprosy, tuberculosis, and highly contagious diseases such as pertussis, respiratory syncytial virus, MERS and SARS. Emphysema, asthma, chronic obstructive pulmonary disease, cystic fibrosis and bronchitis are other lung diseases. In GI mucosa, widespread diseases such as cholera are known to cause between 3 and 5 million new cases annually (NIAID). Sexually transmitted diseases such as gonorrhea, chlamydia (Becker 1996), and syphilis are also a great concern for health of the urogenital mucosal epithelial cells, including vaginal and rectal tissues (NIAID). It is contemplated that the transkingdom NA delivery system taught herein can be used in the treatment of these diseases through the delivery of targeting shRNAs.

Many different diseases specifically affect the mucosal epithelium of different tissue types and addressing pathogen replication in these sites provides options for therapeutic treatment. This delivery platform has the potential to deliver therapeutic NAs to a wide range of mucosal epithelial tissues. Therefore, in addition to improving the transkingdom NA delivery vehicles' properties, we demonstrate the feasibility of delivering these vehicles to several clinically relevant mucosal epithelial tissues that are susceptible to disease. These tissues include the upper/lower respiratory, oral, GI, vaginal, rectal and ocular epithelium.

The platform taught herein facilitates the delivery of NAs, utilizing an efficient/appropriate dosing application to target a very specific and clinically relevant mucosal epithelial tissue and represents a significant advance in the field of NA-based human medicine. The delivery vehicles can be administered to the nasal cavity for local action, aerosolized for upper and lower respiratory diseases, absorbed in the oral cavity for buccal delivery, ingested for GI adsorption, applied to delicate genital mucosal epithelium, and administered for topical ocular delivery. This technology provides for a safe and effective NA delivery vehicle to mucosal epithelial tissues with enhanced stability, therapeutic potency, and overall improved functional properties. This transkingdom NA delivery platform is a significant advance in the field of NA therapeutics and has tremendous therapeutic application while addressing a vast number of diseases that affect a wide range of clinically relevant tissues.

Glossary of Claim Terms

The term "administration" and variants thereof (e.g., "administering" a compound) in reference to a compound of the invention means introducing the compound into the system of the subject in need of treatment. When a compound of the invention is provided in combination with one or more other active agents (e.g., an AIV vaccine, etc.), "administration" and its variants are each understood to include concurrent and sequential introduction of the compound and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to a viral infection, an effective amount comprises an amount sufficient to prevent contracting the disease or to reduce the severity of the disease as evidenced by clinical disease, clinical symptoms, viral titer or virus shedding from the subject, or as evidenced by the ability to prevent or reduce transmission between animals. In some embodiments, an effective amount is an amount sufficient to delay onset of clinical illness and/or symptoms or to prevent the disease. In some embodiments, an effective amount is an amount sufficient to lower viral titers and/or reduce viral shedding. An effective amount can be administered in one or more doses.

As used herein, "treatment" refers to obtaining beneficial or desired clinical results. Beneficial or desired clinical results include, but are not limited to, any one or more of: alleviation of one or more symptoms, diminishment of extent of viral infection, stabilized (i.e., not worsening) state of viral infection, preventing or delaying spread (e.g., shedding) of the viral infection, preventing, delaying or slowing of viral infection progression, and/or maintain weight/weight gain. The methods of the invention contemplate any one or more of these aspects of treatment.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "invasive" when referring to a microorganism, e.g., a bacterium or bacterial therapeutic particle (BTP), refers to a microorganism that is capable of delivering at least one molecule, e.g., an RNA or RNA-encoding DNA molecule, to a target cell. An invasive microorganism can be a microorganism that is capable of traversing a cell membrane, thereby entering the cytoplasm of said cell, and delivering at least some of its content, e.g., RNA or RNA-encoding DNA, into the target cell. The process of delivery of the at least one molecule into t et cell preferably does not significantly modify the invasion apparatus.

As used herein, the term "transkingdom" refers to a delivery system that uses bacteria (or another invasive microorganism) to generate nucleic acids and deliver the nucleic acids intracellularly (i.e. across kingdoms: prokaryotic to eukaryotic, or across phyla: invertebrate to vertebrate) within target tissues for processing without host genomic integration.

Invasive microorganisms include microorganisms that are naturally capable of delivering at least one molecule to a target cell, such as by traversing the cell membrane, e.g., a eukaryotic cell membrane, and entering the cytoplasm, as well as microorganisms which are not naturally invasive and which have been modified, e.g., genetically modified, to be invasive. In another preferred embodiment, a microorganism that is not naturally invasive can be modified to become invasive by linking the bacterium or BTP to an "invasion factor", also termed "entry factor" or "cytoplasm-targeting factor". As used herein, an "invasion factor" is a factor, e.g., a protein or a group of proteins which, when expressed by a non-invasive bacterium or BTP, render the bacterium or BTP invasive. As used herein, an "invasion factor" is encoded by a "cytoplasm-targeting gene". Invasive microorganisms have been generally described in the art, for example, U.S. Pat. Pub. Nos. US 20100189691 A1 and US20100092438 A1 and Xiang, S. et al., *Nature Biotechnology* 24, 697-702 (2006). Each of which is incorporated by reference in its entirety for all purposes.

In a preferred embodiment the invasive microorganism is *E. coli*, as taught in the examples of the present application. However, it is contemplated that additional microorganisms could potentially be adapted to perform as transkingdom delivery vehicles for the delivery of NA. These non-virulent and invasive bacteria and BTPs would exhibit invasive properties, or would be modified to exhibit invasive properties, and may enter a host cell through various mechanisms. In contrast to uptake of bacteria or BTPs by professional phagocytes, which normally results in the destruction of the bacterium or BTP within a specialized lysosome, invasive bacteria or BTP strains have the ability to invade non-phagocytic host cells. Naturally occurring examples of such intracellular bacteria are *Yersinia, Rickettsia, Legionella, Brucella, Mycobacterium, Helicobacter, Coxiella, Chlamydia, Neisseria, Burkolderia, Bordetella, Borrelia, Listeria, Shigella, Salmonella, Staphylococcus, Streptococcus, Porphyromonas, Treponema,* and *Vibrio*, but this property can also be transferred to other bacteria or BTPs such as *E. coli, Lactobacillus, Lactococcus,* or *Bifidobacteriae*, including probiotics through the transfer of invasion-related genes (P. Courvalin, S. Goussard, C. Grillot-Courvalin, C. R. Acad. Sci. Paris 318, 1207 (1995)). Factors to be considered or addressed when evaluating additional bacterial species as candidates for use as transkingdom NA delivery vehicles include the pathogenicity, or lack thereof, of the candidate, the tropism of the candidate bacteria for the target cell, or, alternatively, the degree to which the bacteria can be engineered to deliver NA to the interior of a target cell, and any synergistic value that the candidate bacteria might provide by triggering the host's innate immunity.

Nucleic acids are defined as deoxyribonucleic acids (DNA), ribonucleic acids (RNA), or any closely related compound. They can be coding or non-coding, synthetically or naturally derived, single or double-stranded segments, often consist of molecules of many (2 or more) nucleotides linked. Examples include and are not limited to small interfering RNA/short hairpin RNA (siRNA/shRNA), micro RNA (miRNA), antagomiRs, RNA or DNA aptamers, messenger RNA (mRNA), splice-switching oligonucleotides, antisense oligonucleotides, antigene oligonucleotides, DNAzymes, RNA decoys, ribozymes, peptide nucleic acids, oligomers, and defective interfering particles.

Therapeutic nucleic acids are NAs as described herein or a closely related chemical compound used to treat disease, study disease, or used to achieve a desired genetic modification or used for gene transfer purposes. They are used in cases where specific inhibition or interruption or altering of the function of a particular gene or other molecule involved in disease is thought to be therapeutically desirable.

As used herein, a disease is prevented before or after exposure to the disease, if (1) a medicament composition is administered to a subject internally (by ingestion, inhalation, injection, etc.), topically (on the skin for absorption into the body), or otherwise, and (2) the medicament composition prevents the subject from contracting the disease and experiencing symptoms/clinical illness normally associated with the disease, or, if the subject contracts the disease and experiences or doesn't experience in varying degrees of severity some or all of the symptoms/clinical disease normally associated with the disease, the subject recovers from the disease to a normal healthy state.

Kits for practicing the methods of the invention are further provided. By "kit" is intended any manufacture (e.g., a package or a container) comprising at least one reagent, e.g., a pH buffer of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

In an advantageous embodiment, the kit containers may further include a pharmaceutically acceptable carrier. The kit may further include a sterile diluent, which is preferably stored in a separate additional container. In another embodiment, the kit further comprising a package insert comprising printed instructions directing the use of a combined treatment of a pH buffer and the anti-pathogen agent as a method for treating and/or preventing disease in a subject. The kit may also comprise additional containers comprising additional anti-pathogen agents (e.g. amantadine, rimantadine and oseltamivir), agents that enhance the effect of such agents, or other compounds that improve the efficacy or tolerability of the treatment. A kit could also include at least one reagent that is used to perform a particular conventional technique that are within the skill of the art (i.e. nucleic acid extraction).

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the examples herein above. However, other equivalent conventional procedures can, of course, also be used. Such conventional techniques and descriptions can be found in standard laboratory manuals such as *Genome Analysis: A Laboratory Manual Series* (*Vols. I-IV*), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995) *Biochemistry* (4th Ed.) Freeman, N.Y., Gait, *"Oligonucleotide Synthesis: A Practical Approach"* 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry,* $5^{th}$ Ed., W.H. Freeman Pub., New York, N.Y., all of which are herein incorporated in their entirety by reference for all purposes.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A bacterium for nucleic acid delivery to a eukaryotic cell comprising:
   a nonpathogenic bacterium, wherein the bacterium has been engineered to express at least one invasion factor from a sequence on the chromosome of the bacterium and wherein the bacterium comprises a plasmid having a length less than 4,700 base pairs, the plasmid comprising one or more sequences encoding one or more therapeutic nucleic acids and a prokaryotic promoter to control transcription of the therapeutic nucleic acids.

2. The bacterium for nucleic acid delivery to a eukaryotic cell according to claim 1 wherein the plasmid consists essentially of one or more sequences encoding one or more therapeutic nucleic acids, a sequence encoding a selection marker, an origin of replication, and one or more prokaryotic promoters.

3. The bacterium for nucleic acid delivery to a eukaryotic cell according to claim 1 wherein the plasmid comprises a plurality of therapeutic nucleic acid sequences and a plurality of prokaryotic promoters, wherein a first therapeutic nucleic acid sequence is under the control of a first prokaryotic promoter and a second therapeutic nucleic acid sequence is under the control of a second prokaryotic promoter.

4. The bacterium for nucleic acid delivery to a eukaryotic cell according to claim 1 wherein the first prokaryotic promoter is a different promoter than the second prokaryotic promoter, whereby having, different prokaryotic promoters allows for differential transcription of one or more of the plurality of therapeutic nucleic acid sequences.

5. The bacterium for nucleic acid delivery to a eukaryotic cell according to claim 1 wherein the therapeutic nucleic acid is a small interfering RNA/short hairpin RNA (siRNA/shRNA).

6. The bacterium for nucleic acid delivery to a eukaryotic cell according to claim 1 wherein the therapeutic nucleic acid is a nucleic acid selected from the group consisting of micro RNA (miRNA), miRNA mimics and inhibitors, antagomiRs, RNA or DNA aptamers, messenger RNA (mRNA), splice-switching oligonucleotides, antisense oligonucleotides, antigene oligonucleotides, DNAzymes, RNA decoys, ribozymes, peptide nucleic acids, oligomers, and defective interfering particles.

7. The bacterium for nucleic acid delivery to a eukaryotic cell according to claim 1 wherein the bacterium is an engineered bacterium from the group of bacteria consisting of *Listeria, Yersinia, Rickettsia, Shigella, E. coli, Salmo-* nella, Legionella, Chlamydia, Brucella, Neisseria, Burkolderia, Bordetella, Borrelia, Coxiella, Mycobacterium, Helicobacter, Staphylococcus, Streptococcus, Porphyromonas, Vibrio, Treponema, Lactobacillus, and Bifidobacteria.

8. The bacterium for nucleic acid delivery to a eukaryotic cell according to claim 1 wherein the bacterium is engineered to express an Inv protein or a fragment or binding domain thereof from a sequence on the chromosome of the bacterium or the bacterium is engineered to express an influenza hemagglutinin-1 (HA-1) protein or a fragment or binding domain thereof from a sequence on the chromosome of the bacterium.

9. The bacterium for nucleic acid delivery to a eukaryotic cell according to claim 1 wherein the bacterium has a selection marker that has a plurality of selection marker elements and the bacterium has been engineered to express at least one of the selection marker elements from a sequence on the chromosome of the bacterium.

10. The bacterium for nucleic acid delivery to a eukaryotic cell according to claim 1 wherein the invasion factor is encoded by a gene selected from the group consisting of an inv gene, a hlyA gene, an HA-1 gene or combinations thereof.

11. The bacterium for nucleic acid delivery to a eukaryotic cell according to claim 1 wherein the therapeutic nucleic acid interferes with one or more target influenza virus RNA molecules.

12. The bacterium for nucleic acid delivery to a eukaryotic cell according to claim 1 wherein the therapeutic nucleic acid interferes with one or more viruses selected from the group consisting of coronavirus, Herpes simplex virus types 1 and 2 (HSV-1 and HSV-2), Human papillomavirus (HPV), respiratory syncytial virus, MERS and SARS.

13. The bacterium for nucleic acid delivery to a eukaryotic cell according to claim 1 wherein the bacterium is engineered to express a protein that binds a sialic acid residue on a target cell from a sequence on the chromosome of the bacterium.

14. The bacterium for nucleic acid delivery to a eukaryotic cell according to claim 1 wherein the bacterium is engineered to express a binding domain from a coronavirus, norovirus, rotavirus, mumps virus, parainfluenza, *Clostridium botulinum*, or *Vibrio cholera.*

15. A bacterium for nucleic acid delivery to a eukaryotic cell comprising:

a nonpathogenic bacterium, wherein the bacterium has been engineered to express LLO, INV, or HA-1 from a sequence on the chromosome of the bacterium and wherein the bacterium comprises a plasmid having a length less than 4,700 base pairs, the plasmid comprising one or more sequences encoding one or more therapeutic nucleic acids and a prokaryotic promoter to control transcription of the therapeutic nucleic acids.

16. The bacterium for nucleic acid delivery to a eukaryotic cell according to claim 15 wherein the plasmid consists essentially of one or more sequences encoding one or more therapeutic nucleic acids, a sequence encoding a selection marker, an origin of replication, and one or more prokaryotic promoters.

17. The bacterium for nucleic acid delivery to a eukaryotic according to claim 15 wherein the plasmid comprises a plurality of therapeutic nucleic acid sequences and a plurality of prokaryotic, promoters, wherein a first therapeutic nucleic acid sequence is under the control of a first prokaryotic promoter and a second therapeutic nucleic acid sequence is under the control of a second prokaryotic promoter.

18. The bacterium for nucleic acid delivery to a eukaryotic according to claim 15 wherein the first prokaryotic promoter is a different promoter than the second prokaryotic promoter, whereby having different prokaryotic promoters allows for differential transcription of one or more of the plurality of therapeutic nucleic acid sequences.

19. The bacterium for nucleic acid delivery to a eukaryotic cell according to claim 15 wherein the therapeutic nucleic acid is a small interfering RNA/short hairpin RNA (siRNA/shRNA).

20. The bacterium for nucleic acid delivery to a eukaryotic cell according to claim 15 wherein the therapeutic nucleic acid is a nucleic acid selected from the group consisting of micro RNA (miRNA), miRNA mimics and inhibitors, antagomiRs, RNA or DNA aptamers, messenger RNA (mRNA), splice-switching oligonucleotides, antisense oligonucleotides, antigene oligonucleotides, DNAzymes, RNA decoys, ribozymes, peptide nucleic acids, oligomers, and defective interfering particles.

21. The bacterium for nucleic acid delivery to a eukaryotic c ell according to claim 15 wherein the selection marker has a plurality of selection marker elements and the bacterium has been engineered to express at least one of the selection marker elements from a sequence on the chromosome of the bacterium.

22. The bacterium for nucleic acid delivery to a eukaryotic cell according to claim 15 wherein the bacterium is an engineered bacterium from the group of bacteria consisting of *Listeria, Yersinia, Rickettsia, Shigella, E. coli, Salmonella, Legionella, Chlamydia, Brucella, Neisseria, Burkolderia, Bordetella, Borrelia, Coxiella, Mycobacterium, Helicobacter, Staphylococcus, Streptococcus, Porphyromonas, Vibrio, Treponema, Lactobacillus*, and *Bifidobacteria.*

23. The bacterium for nucleic acid delivery to a eukaryotic cell according to claim 15 wherein the therapeutic nucleic acid interferes with one or more target influenza virus RNA molecules.

24. The bacterium for nucleic acid delivery to a eukaryotic cell according to claim 15 wherein the therapeutic nucleic acid interferes with one or more viruses selected from the group consisting of coronavirus, Herpes simplex virus types 1 and 2 (HSV-1 and HSV-2), Human papillomavirus (HPV), respiratory syncytial virus, MERS and SARS.

25. The bacterium for nucleic acid delivery to a eukaryotic cell according to claim 15 wherein the bacterium is engineered to express a binding domain from a coronavirus, norovirus, rotavirus, mumps virus, parainfluenza, *Clostridium botulinum*, or *Vibrio cholera.*

26. A kit for nucleic acid delivery to a eukaryotic cell comprising:

a nonpathogenic bacterium, wherein the bacterium has been engineered to express at least one invasion factor from a sequence on the chromosome of the bacterium; and a plasmid having a length less than 4,700 base pairs, the plasmid comprising, a cloning site for one or more sequences encoding one or more therapeutic nucleic acids, and a prokaryotic promoter, wherein the prokaryotic promoter controls transcription for the cloning site.

27. A bacterium for nucleic acid delivery to a eukaryotic cell comprising:
a nonpathogenic bacterium, wherein the bacterium has been engineered to express at least one invasion factor from a sequence on the chromosome of the bacterium and wherein the bacterium comprises a plasmid consisting essentially of one or more sequences encoding one or more therapeutic nucleic acids, an origin of replication, a sequence encoding a selection marker, and one or more prokaryotic promoters to control transcription of the nucleic acids.

28. The bacterium for nucleic acid delivery to a eukaryotic cell according to claim 27 wherein the selection marker has a plurality of selection marker elements and the bacterium has been engineered to express at least one of the selection marker elements from a sequence on the chromosome of the bacterium.

29. The bacterium for nucleic acid delivery to a eukaryotic cell according to claim 27 wherein the plasmid has a length less than 4,700 base pairs.

\* \* \* \* \*